(12) United States Patent
Lee et al.

(10) Patent No.: US 9,238,006 B2
(45) Date of Patent: Jan. 19, 2016

(54) COMPOSITION CONTAINING INORGANIC NANOPARTICLES AS AN ACTIVE INGREDIENT FOR PREVENTING OR TREATING OF ANGIOGENESIS-RELATED DISEASES

(71) Applicant: KOREA RESEARCH INSTITUTE OF STANDARDS AND SCIENCE, Daejeon (KR)

(72) Inventors: Tae Geol Lee, Daejeon (KR); Jeong Hun Kim, Seoul (KR); Dong Hyun Jo, Seoul (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 94 days.

(21) Appl. No.: 13/623,497

(22) Filed: Sep. 20, 2012

(65) Prior Publication Data

US 2014/0044753 A1     Feb. 13, 2014

(30) Foreign Application Priority Data

Aug. 7, 2012   (KR) .................. 10-2012-0086044

(51) Int. Cl.

| | |
|---|---|
| *A61K 9/14* | (2006.01) |
| *A61K 33/24* | (2006.01) |
| *A61K 33/00* | (2006.01) |
| *A61P 27/02* | (2006.01) |
| *A61P 9/10* | (2006.01) |
| *C01G 23/047* | (2006.01) |
| *B82Y 5/00* | (2011.01) |
| *C01B 33/18* | (2006.01) |

(52) U.S. Cl.
CPC . *A61K 9/14* (2013.01); *A61K 33/00* (2013.01); *A61K 33/24* (2013.01); *C01B 33/18* (2013.01); *B82Y 5/00* (2013.01); *Y10T 428/2982* (2015.01)

(58) Field of Classification Search
None
See application file for complete search history.

(56) References Cited

U.S. PATENT DOCUMENTS

| 6,270,749 | B1 * | 8/2001 | Blumenkranz et al. ...... 424/9.61 |
| 2002/0127224 | A1 * | 9/2002 | Chen .......................... 424/130.1 |
| 2005/0003014 | A1 * | 1/2005 | Ketelson et al. .............. 424/489 |
| 2009/0137999 | A1 * | 5/2009 | Silberberg et al. ............ 606/15 |
| 2010/0323023 | A1 * | 12/2010 | Garvey et al. ................. 424/490 |

FOREIGN PATENT DOCUMENTS

JP      2005-538033 A     12/2005

OTHER PUBLICATIONS

Lai et al. Int J Nanomed vol. 5, pp. 715-723, Sep. 18, 2010.*
Ballas and Chachoua Oncotargets and Therapy vol. 4, pp. 43-58, 2011.*
Alessi et al Eur Cytokine Netw vol. 20, pp. 225-233, 2009.*
Paez-Ribes et al Cancer Cell vol. 15, pp. 220-231, 2009.*
Ebos et al. Cancer Cell vol. 15 pp. 232-239, 2009.*
Klement et al., Br. J. Anaesth. vol. 66, No. 2, pp. 189-195, publication year: 1991.*
Ferin et al. Am J. Respir. Cell Mol. Biol vol. 6, pp. 535-542. publication year: 1992.*
Dong Hyun Jo, et al., "Antiangiogenic effect of silicate nanoparticle on retinal neovascularization induced by vascular endothelial growth factor", Nanomedicine: Nanotechnology, Biology, and Medicine, 2012, pp. 784-791, vol. 8.
Kim et al., "The Inhibition of Retinal Neovascularization by Gold Nanoparticles via Suppression of VEGFR-2 Activation," Biomaterials, 2011, vol. 32, pp. 1865-1871.
Yoon et al., "Susceptibility Constants of *Escherichia coli* and *Bacillus subtilis* to Silver and Copper Nanoparticles," Science of the Total Environment, 2007, vol. 373, pp. 572-575.
Aiello et al., "Vascular Endothelial Growth Factor in Ocular Fluid of Patients with Diabetic Retinopathy and Other Retinal Disorders," The New England Journal of Medicine, 1994, vol. 331, pp. 1480-1487.
Werner Risau, "Mechanisms of Angiogenesis," Nature, 1997, vol. 386, pp. 671-674.
Kemp et al., "Gold and Silver Nanoparticles Conjugated with Heparin Derivative Possess Anti-Angiogenesis Properties," Nanotechnology, 2009, vol. 20, pp. 1-7.

* cited by examiner

*Primary Examiner* — Richard Schnizer
*Assistant Examiner* — Katherine Peebles
(74) *Attorney, Agent, or Firm* — Sughrue Mion, PLLC

(57) ABSTRACT

Provided is a pharmaceutical composition containing inorganic nanoparticles selected from titanium oxide nanoparticles or silica nanoparticles as an active ingredient for preventing or treating angiogenesis-related diseases. The pharmaceutical composition for preventing or treating angiogenesis-related diseases according to the present invention may be used as a therapeutic agent for various diseases based on angiogenesis such as age-related macular degeneration, tumors, and diabetes-related complications.

3 Claims, 16 Drawing Sheets

US 9,238,006 B2

COMPOSITION CONTAINING INORGANIC NANOPARTICLES AS AN ACTIVE INGREDIENT FOR PREVENTING OR TREATING OF ANGIOGENESIS-RELATED DISEASES

CROSS-REFERENCE TO RELATED APPLICATIONS

This application claims priority under 35 U.S.C. §119 to Korean Patent Application No. 10-2012-0086044, filed on Aug. 7, 2012, in the Korean Intellectual Property Office, the disclosure of which is incorporated herein by reference in its entirety.

TECHNICAL FIELD

The following disclosure relates to a pharmaceutical composition containing inorganic nanoparticles as an active ingredient for preventing or treating angiogenesis-related diseases. More particularly, the following disclosure relates to a pharmaceutical composition containing inorganic nanoparticles selected from titanium oxide ($TiO_2$) nanoparticles or silica nanoparticles (SiNP, Si Nanoparticle) as an active ingredient for treating angiogenesis-related diseases.

BACKGROUND

Angiogenesis is a biological process of supplying new blood vessels to tissue or organ, and more particularly, means the formation of new capillary blood vessels from pre-existing capillary blood vessels, which is a basic process of forming blood vessels in a body after growth. The process of forming new blood vessels is a significantly complicated and delicate procedure, and is briefly described as follows. First, when a stimulus for angiogenesis is transmitted to the pre-existing blood vessels, the vessels are expanded and blood vessel permeability is increased. Second, fibrin is released to the outside of the vessel through the expanded vessel to be deposited in a cytoplasmic matrix around the vessel. Third, enzymes for degrading a basement membrane of pre-existing vessels are activated, the basement membranes are degraded, and endothelial cells are released between the degraded basements to be proliferated in matrix of neighboring cells and migrated. Finally, endothelial cells arranged in a row form shape of a vessel, such that a new blood vessel is generated (Risau, W. (1997) Nature: 386 671-674).

The process of angiogenesis is strictly regulated by various negative and positive regulators (Folkman and Cotran., Int. Rev. Exp. Patho., 16, 207~248, 1976). When angiogenesis is abnormally regulated, various diseases such as cancer, rheumatoid arthritis, diabetic retinopathy, or the like, occur. Particularly, in the case in which this pathological angiogenesis is generated in retina, the angiogenesis causes retinal edema, retinal or vitreous hemorrhage, and finally traction retinal detachment. In addition, the angiogenesis in the retina becomes a major cause of retinopathy of prematurity (ROP), diabetic retinopathy (DR), and age-related macular degeneration (AMD) (Aiello L P, et al., N. Engl. J. Med., 1994, 331, 1480-1487).

Recently, nanoparticles (NPs) have been widely used for industrial and biomedical objects. Particularly, the nanoparticles have been suggested as a selective drug delivery system (P. S. Ghosh, C. K Kim, G. Han, N. S. Forbes, V. M. Rotello, ACS Nano 2008, 2, 2213.) and a potential antibacterial drug against bacterial infection (K.Y.Yoon, J. H. Byeon, J. H. Park, J. Hwang, Sci. Total. Environ. 2007, 373:572.). In addition, it was reported that gold or silver nanoparticles inhibit the angiogenesis induced by vascular endothelial growth factor (VEGF), and researches into development of an angiogenesis inhibitor using the nanoparticle have been conducted. However, in order to use the nanoparticle in treatment, careful evaluation of toxicity of the nanoparticle and effort to minimize the toxicity are necessarily required. That is, development of a nanoparticle therapeutic agent of excellent effect and low toxicity has been requested.

Therefore, the present inventors discovered that inorganic nanoparticles selected from titanium oxide nanoparticles or silica nanoparticles have anti-angiogenic effect at a concentration at which the nanoparticles do not have the toxicity, and completed the present invention.

RELATED ART DOCUMENT

Non-Patent Document

1. Jin Hyung Kim, et al. The Inhibition of Retinal Neovascularization by Gold Nanoparticles Via Inhibition of VEGFR-2 Activation. Biomaterials 32 (2011), 1865-1871.
2. Kemp M M, et al. Gold and Silver Nanoparticles Conjugated With Heparin Derivative Possess Anti-Angiogenesis Properties. Nanotechnology 2009; 20:455104.

SUMMARY

An embodiment of the present invention is directed to providing a pharmaceutical composition containing inorganic nanoparticles selected from titanium oxide nanoparticles or silica nanoparticles as an active ingredient for preventing or treating angiogenesis-related diseases.

Another embodiment of the present invention is directed to providing a therapeutic agent for the angiogenesis-related diseases containing the pharmaceutical composition.

In one general aspect of the present invention, there is provided a pharmaceutical composition containing inorganic nanoparticles selected from titanium oxide nanoparticles or silica nanoparticles as an active ingredient for preventing or treating angiogenesis-related diseases.

In the present invention, the term "prevention" means all actions of inhibiting or delaying generation, diffusion, or recurrence of cancer diseases or angiogenesis-related diseases, and the term "treatment" means all actions of improving symptoms of the disease or being advantageously changed due to administration of the composition according to the present invention.

In the present invention, the term "angiogenesis" means a process of forming new blood vessels, that is, a process in which new blood vessels are generated in cell, tissue, or organ, and the term "neovascularization" means new blood vessels formed through the angiogenesis. In the present invention, the terms "angiogenesis" and "neovascularization" may be compatibly used with each other.

In the present invention, the term "angiogenesis-related diseases" means diseases caused by abnormal formation of new blood vessels as described above.

Diseases or a state capable of being prevented or treated by the pharmaceutical composition according to the present invention include various diseases related to the angiogenesis. Preferable examples of the disease capable of being prevented or treated by the pharmaceutical composition according to the present invention include cancer, diabetic retinopathy, retinopathy of prematurity, age-related macular degeneration, corneal graft rejection, neovascular glaucoma, erythrosis, proliferative vitreoretinopathy, psoriasis, hemophilic joints, capillary proliferation in atherosclerosis plaque, keloid, wound granulation, vascular adhesion, rheumatoid arthritis, osteoarthritis, autoimmune disease, Crohn's disease, recurrent stenosis, atherosclerosis, enterostenosis, Cat scratch disease, ulcers, hepatic cirrhosis, glomerulonephritis, diabetic nephropathy, malignant nephrosclerosis, thrombotic microangiopathy, organ transplant rejection, glomerulopathy, diabetes, inflammation, or neurodegenerative diseases, but are not limited thereto.

More preferable examples of the disease capable of being prevented or treated by the pharmaceutical composition according to the present invention include diabetic retinopathy, retinopathy of prematurity, and age-related macular degeneration.

In the present invention, the term "nanoparticle" means a particle having a dimension on the nanometer scale, and generally, means a particle having a size of 1 to 100 nm.

In order to use the nanoparticle in the treatment, it is significantly important to carefully evaluate the toxicity of the nanoparticle in vitro and in vivo. In order to solve problems of nanotoxicity, researchers on nanomedicine tend to use nanopaticle of biodegradable polymers. However, metal or other inorganic nanoparticles still have features appropriate and attractive for application in the treatment of various diseases. First, since it is relatively easy to manipulate a size, a surface charge, and a shape of the nanoparticle, the nanoparticle may have high bioavailability and effectiveness. Second, conjugation of ligands and receptors to nanopaticles facilitates the targated therapy. Furthermore, the nanoparticle itself also directly affects biological processes such as angiogenesis, apoptosis, and modulation of oxidative stress. In the research into the angiogenesis, it was found that gold and silver nanoparticles have the property of inhibiting proliferation of endothelial cell induced by VEGF. However, in spite of numerous advantages in a medical field as described above, researchers are hesitant to use the nanoparticles due to several reports about the toxicity of nanoparticles.

It was known that the toxicity of the inorganic nanoparticles depends on a size thereof and a crystal structure thereof. In the case in which the size of the nanoparticle is smaller than 10 nm, nanoparticles seem to have more cytotoxicity, and in the case in which the size of the nanoparticle is larger than 60 nm, nanoparticles are expected to have less anti-angiogenesis effect. It was confirmed that the titanium oxide inorganic nanoparticles or silica inorganic nanoparticles having a size of 10 to 60 nm according to the present invention do not have genetic, cellular, and histological toxicity but have anti-angiogenenic effect. Therefore, the size of the inorganic nanoparticles contained as an active ingredient in the pharmaceutical composition according to the present invention may be 10 to 60 nm.

The concentration of the inorganic nanoparticles contained as an active ingredient in the pharmaceutical composition according to the present invention may be $10^5$ to $10^6$ nanoparticles per cell. In the preferable concentration, the nanoparticles do not have histological, cytological, and genetic toxicity and inhibit the angiogenesis, thereby treating the angiogenesis-related disease.

The pharmaceutical composition inhibits phosphorylation of vascular endothelial growth factor receptor (VEGFR)-2 and activation of extracellular signal-regulated kinase (ERK) 1/2. It was confirmed that the silica or titanium oxide nanoparticles according to the present invention inhibit phosphorylation of VEGFR-2 and also inhibit phosphorylation of ERK1/2 (See FIG. 11).

It was known that the silver nanoparticle affects a phosphatidyl inositol 3-kinase (PI3K)/Akt signaling pathway at a concentration in which the silver particle affects cell survival, but it was confirmed that the silica nanoparticle inhibits a mitogen-activated protein kinase (MAPK)/ERK pathway without inhibiting the phosphorylation of PI3K/Akt pathway as the gold nanoparticle does. In addition, the titanium oxide nanoparticle also inhibited the phosphorylation of VEGFR-2 and the activation of ERK1/2 and did not affect activation of Akt (See FIGS. 12 to 14).

The pharmaceutical composition containing the inorganic nanoparticles selected from the titanium oxide or silica nanoparticles as the active ingredient does not have toxicity to the vascular endothelial cell.

The pharmaceutical composition according to the present invention may not have toxicity to the vascular endothelial cell while inhibiting proliferation and invasion of the vascular endothelial cell to inhibit angiogenesis. It was confirmed that the inorganic nanoparticles, which are the active ingredient of the pharmaceutical composition of the present invention, do not have toxicity at a concentration according to the present invention by analyzing the toxicity of inorganic nanoparticles in vivo and in vitro (See FIGS. 2A to 5B). In addition, it was confirmed that titanium oxide nanoparticles having various crystal structures and sizes do not have photo toxicity to retinal pigment epithelial cells at a concentration of 1 µg/ml even in a state in which ultra violet ray is irradiated, titanium oxide nanoparticle having a size of 28 nm does not induce cytotoxicity in pulmonary epithelial cells at a concentration of 40 µg/ml, and titanium oxide nanoparticles having sizes of 25 nm or less and an anatase structure do not damage DNA at a concentration range of 8 to 800 ng/ml and do not affect viability of human epidermal cells.

The pharmaceutical composition containing the inorganic nanoparticles selected from silica nanoparticles or the titanium oxide nanoparticles as the active ingredient may further contain at least one of a pharmaceutically acceptable excipient, a carrier, or a combination thereof.

Here, the term "pharmaceutically acceptable" means that which is physiologically acceptable and generally, does not cause an allergy reaction such as dizziness, gastric disorder, or reactions similar thereto when the composition is administered to human. The pharmaceutically excipient and carrier contained in the pharmaceutical composition of the present invention are generally used at the time of preparation and contains lactose, dextrose, sucrose, sorbitol, mannitol, starches, acacia rubber, calcium phosphate, alginate, gelatin, calcium silicate, Microcrystalline cellulose, polyvinylpyrrolidone, cellulose, water, syrup, methyl cellulose, methylhydroxybenzoate, propylhydroxybenzoate, talc, magnesium stearate, mineral oil, and the like, but are not limited thereto.

The pharmaceutical composition according to the present invention may further contain a diluent, a lubricant, a wetting agent, a sweetener, a flavoring agent, an emulsifier, a suspending agent, a preservative, or the like, in addition to the above ingredients.

In another general aspect of the present invention, there is provided a therapeutic agent for treating angiogenesis-related diseases containing the pharmaceutical composition of the present invention. The pharmaceutical composition according to the present invention inhibits the angiogenesis in a safe manner for a human, such that the pharmaceutical composition may be used to prevent or treat various angiogenesis-related diseases.

The therapeutic agent for treating the angiogenesis-related disease may be formulated into dosage forms selected from a group consisting of liquid dispersions, gels, aerosols, ointments, creams, controlled release formulations, fast-dissolving dosage form, freeze-dried formulations, tablets, capsules, delayed release formulations, sustained release formulations, pulsatile release formulations, and mixed immediate release and controlled release dosage form.

In addition, the therapeutic agent according to the present invention may further contain adjuvant such as a preservative, a wettable powder, an emulsion promoter, a salt for adjusting osmotic pressure, or buffers and other therapeutically valuable substances and be formulated by a general method. Further, the therapeutic agent according to the present invention may be formulated using the known method in the art so as to provide a rapid, sustained, or delayed release of the active ingredient after administration to mammals and be formulated into various dosage forms for oral or parenteral administration.

A representative example of the formulation for the parenteral administration is a formulation for injection, and may be an isotonic aqueous solution or suspensions for injection. The formulation for injection may be prepared using suitable dispersants, wetting agents, and suspending agents by the known method in the art. For example, each ingredient may be dissolved in saline or buffer solutions to thereby be formulated into the formulation for injection. Further, as the formulation for oral administration, there are oral tablets, buccal tablets, troches, capsules, elixirs, suspensions, syrups, the wafers, and the like, wherein these formulation may contain a diluent (for example, lactose, dextrose, sucrose, mannitol, sorbitol, cellulose and/or glycine) and a lubricant (for example, silica, talc, stearic acid and its magnesium or calcium salt and/or polyethylene glycol) in addition to the active ingredient. The tablet may contain a binder such as magnesium aluminum silicate, starch paste, gelatin, tragacanth, methyl cellulose, sodium carboxymethylcellulose and/or polyvinylpyrrolidone and in some cases, contain a disintegrant, an absorbent, a colorant, a flavoring agent and/or an additional sweetener such as starch, agar, alginic acid or its sodium salt. The formulation may be prepared by a general mixing, granulation, or coating method.

The therapeutic agent according to the present invention may be administered through various routes including an oral, transdermal, subcutaneous, intravenous, intravitreous, subconjunctival, subretinal, topical (skin, eye, mucosal membrane) or an intramuscular route, and dosage of the active ingredient may be properly selected according to various factors such as the administration route, patient's age, gender, weight, and severity of disease of the patients. In addition, the composition according to the present invention may be administered in conjunction with the known compound capable of increasing the effect to be desired. The therapeutic agent according to the present invention may be administered by oral administration or parenteral administration such as intravenous, subcutaneous, nasal, intraperitoneal administration, or the like, to a human and an animal. The oral administration includes sublingual administration. The parenteral administration includes an injection method such as subcutaneous injection, intramuscular injection, and intravenous injection and a dripping method.

BRIEF DESCRIPTION OF THE DRAWINGS

The patent pr application file contains at least one drawing executed in color. Copies of this patent or patent application publication with color drawings will be provided by the Office upon request and payment of the necessary fee.

FIG. 2A is a graph using human retinal microvascular endothelial cells (HRMEC) as a target, and FIG. 2B is a graph using human retinoblastoma cells (SNUOT-Rb1 cells) as a target.

FIGS. 3A and 3B are graphs showing viabilities of cells treated with each concentration of silica nanoparticles, wherein FIG. 3A is a graph using SNUOT-Rb1 cells as a target, and FIG. 3B is a graph using HRMEC cells as a target.

FIGS. 4A and 4B show influences of the nanoparticles on apoptosis through terminal deoxynucleotidyl transferase dUTP nick end labeling (TUNEL) assay, wherein FIG. 4A shows an influence of the titanium oxide nanoparticles and FIG. 4B shows an influence of the silica nanoparticles.

FIGS. 5A and 5B are results obtained by evaluating influences of nanoparticles on a thickness and structure of the retina, wherein FIG. 5A is a result of the titanium oxide nanoparticles and FIG. 5B is a result of the silica nanoparticles.

FIGS. 6A and 6B are results obtained by confirming whether the titanium oxide nanoparticles have inhibitory effect on retinal angiogenesis in oxygen-induced retinopathy model, wherein FIG. 6A is a photograph of tissue dyed using hematoxylin and eosin, and FIG. 6B is a graph showing results obtained by observing 10 fragments or more by an optical microscope.

FIGS. 8A and 8B show that titanium oxide nanoparticles inhibit tube formation and migration of endothelial cells, wherein FIG. 8A is an optical microscope photograph, and FIG. 8B is a graph showing quantitative assay for the number of connected cells and the number of migrated cells.

FIGS. 13A and 13B show that the silica nanoparticles inhibit the phosphorylation of the VEGFR-2 in the retinal endothelial cell, wherein FIG. 13A is a western blotting result for VEGFR-2, and FIG. 13B is a western blotting result for ERK1/2.

DETAILED DESCRIPTION OF EMBODIMENTS

Hereinafter, the present invention will be described in more detail by the following Examples.

However, the following Examples are to illustrate the present invention, and the scope of the present invention is not limited to Inventive Examples.

EXAMPLE 1

Preparation of Nanoparticle

1. Separation of titanium oxide nanoparticle In order to use nanoparticles having a specific size, nanoparticles having a size of 20 nm were isolated from P25 titanium oxide nanoparticles ($TiO_2$ nanoparticles) (77% anatase and 23% rutile, Degussa/Evonik, Dusseldorf, Germany). Since the P25 $TiO_2$ powder may be easily aggregated in an aqueous solution state, several separation steps was required. In order to prepare well dispersed $TiO_2$ in water, stirring, ultrasonication, and high speed centrifugation were performed in order.

Figure 1:
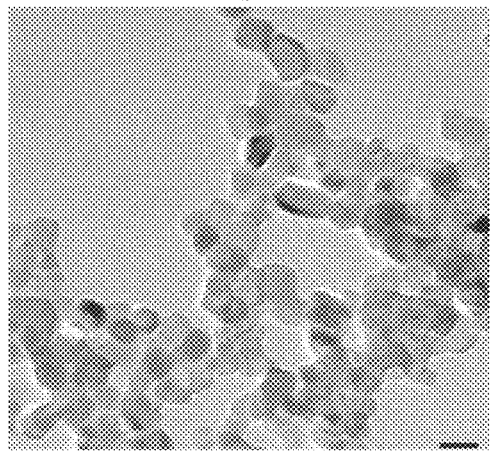
FIG. 1 is a transmission electron microscope photograph of titanium oxide nanoparticles used in experiments. (The scale bar indicates 20 nm.).
Figure 2A:
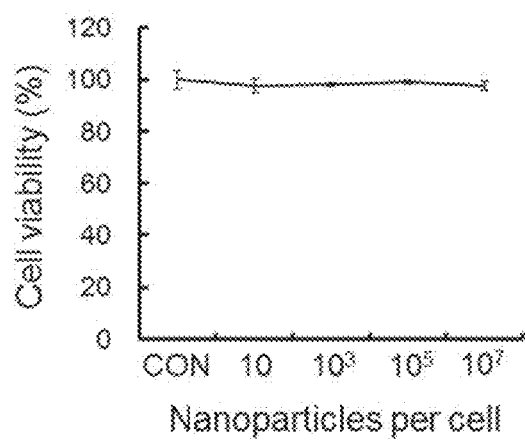
FIGS. 2A and 2B are graphs showing cell viabilities of the cell treated with the titanium oxide nanoparticles having various concentrations. Here.
Figure 2B:
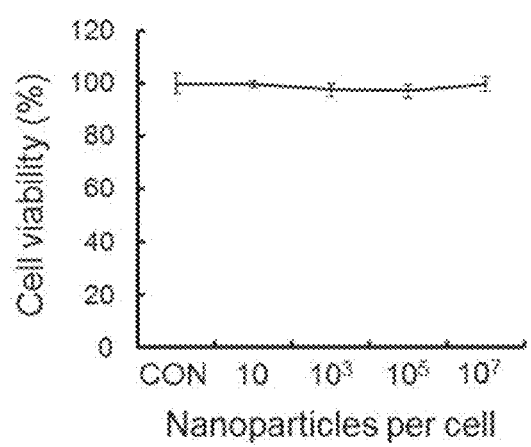
Figure 3A:
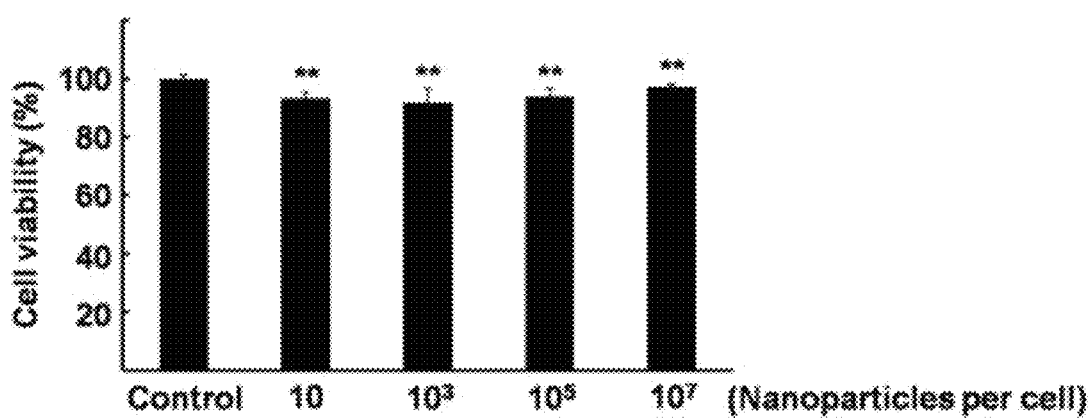
Figure 3B:
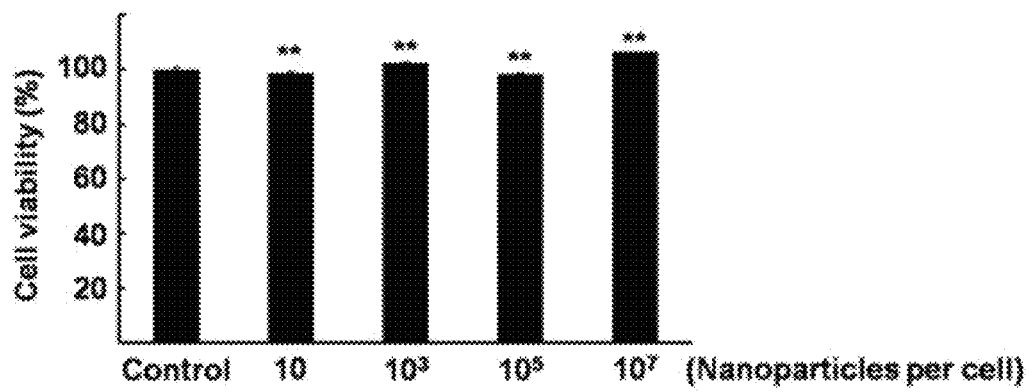

As the result of analyzing the separated particles using a transmission electronic microscope, an average size (diameter) of the nanoparticles was 18.37±5.66 nm (See FIG. 1).

2. Synthesis of Silica Nanoparticle (SiNP)

The SiNP was synthesized by the known reverse micro emulsion method. 16 mg of L-arginine was dissolved in 40 ml of water as a catalyst, and in order to maintain the aqueous solution state, 3 ml of cyclohexane and 3 ml of TEOS were added thereto. An organic phase containing a precursor of the SiNP was transferred to an aqueous phase by hydrolysis and condensation reactions. Then, in order to form spherical silica particles, the solution was slowly stirred for 24 hours at 70° C. Next, in order to obtain water dispersible SiNP, the organic phase was removed. A transmission electron microscopy (TEM) image of the SiNP was obtained using a FE-STEM (HD-2300A, Hitachi, Tokyo, Japan), and a size and size distribution of SiNP were analyzed by the TEM image based on Image J program.

The overall particle size of the SiNP was 57 nm (57.26±7.07 nm).

In order to perform another analysis, the nanoparticles were used in a state in which they were dispersed in distilled water (pH 8.2). In order to treat cells with the nanoparticles, stock solution was prepared, and the stock solution was diluted with culture medium to treat the same number of cells with the same number of nanoparticles.

EXAMPLE 2

Toxicity Assay of Nanoparticle

1. Cytotoxicity Analysis-Cell Viability Assay

In order to analyze an influence of the inorganic nanoparticles on cell viability, MTT assay was performed.

Human retinal microvascular endothelial cells (HRMEC), SNUOT-Rb1 cells ($4\times10^3$ cells), which are human retinoblastoma cells, and human brain astrocytes were plated into 96-well plates, and were cultured overnight. Next, cells in each well were treated with a concentration of 10, $10^3$, $10^5$, $10^7$ SiNPs and $TiO_2$ nanoparticles (per cells) for 48 hours, followed by replacing with fresh culture media containing 0.5 mg/ml MTT, and then were incubated in an atmosphere of 95% air and 5% $CO_2$ for 4 hours at 37° C. Then the culture media were removed, and 200 μl of DMSO was treated to each well. Optical density (OD) was measured at 560 nm using a microplate reader (Molecular Devices, Inc., Sunnyvale, Calif., USA).

As a result, the nanoparticles did not affect the survival of HRMEC, SNUOT-Rb1 cells, and human brain astrocytes in the above concentration range, and even $10^7$ nanoparticles did not have cytotoxicity (See FIGS. 2A to 3B).

2. Histological Toxicity Evaluation

In order to evaluate histological toxicity of the inorganic nanoparticles, terminal deoxynucleotidyl transferased UTP nick end labeling (TUNEL) assay was performed.

In order to evaluate histological toxicity induced by the inorganic nanoparticle, the titanium oxide nanoparticles (1 μl) were injected into the right eye of 8 week old mice (female C57BL/6J mice) at a concentration of 1.30 μg/ml corresponding to 10 times of a presumptive therapeutic concentration thereof, and the SiNPs (1 μl) were injected at a concentration of 1 mg/ml corresponding to 100 times of a presumptive therapeutic concentration thereof. After 7 days, the eyes were enucleated from the mice. The enucleated eyes were immersed in a 4% formalin solution, and then were embedded in paraffin. A serial paraffin section having a thickness of 4 μm was obtained from a paraffin block. In the paraffin sections, paraffin was deparaffined and hydrated by sequential immersion in xylene and graded ethanol soultion. The section obtained for histological analysis was stained with hematoxylin and eosin. For TUNEL assay, TUNEL labeling was performed using a fluorescein kit (Roche, Basel, Switzerland), and a TUNEL-positive cell was analyzed in 10 fields randomly selected from each slide using a fluorescence microscope at a magnification of 400× (Olympus Corp., Tokyo, Japan).

Figure 4A:
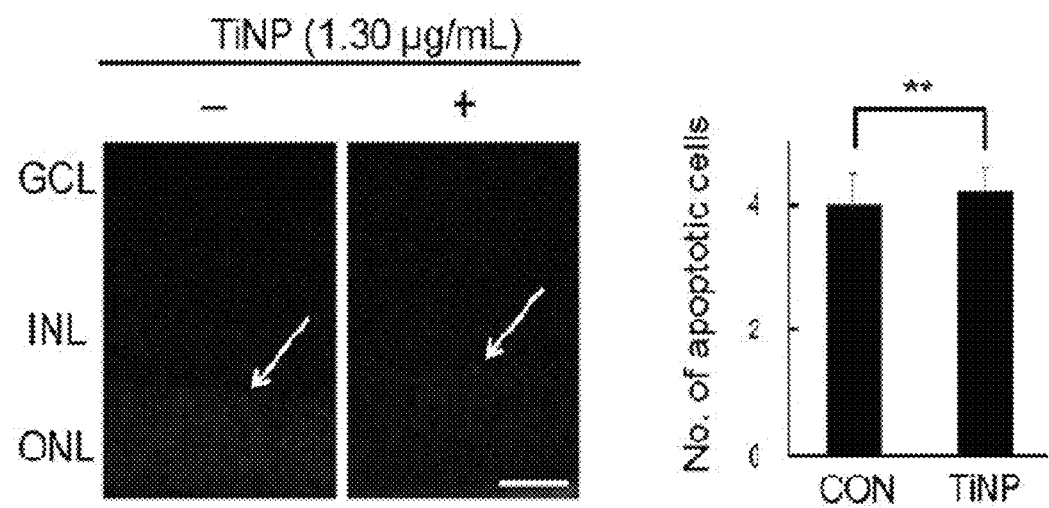
Figure 4B:
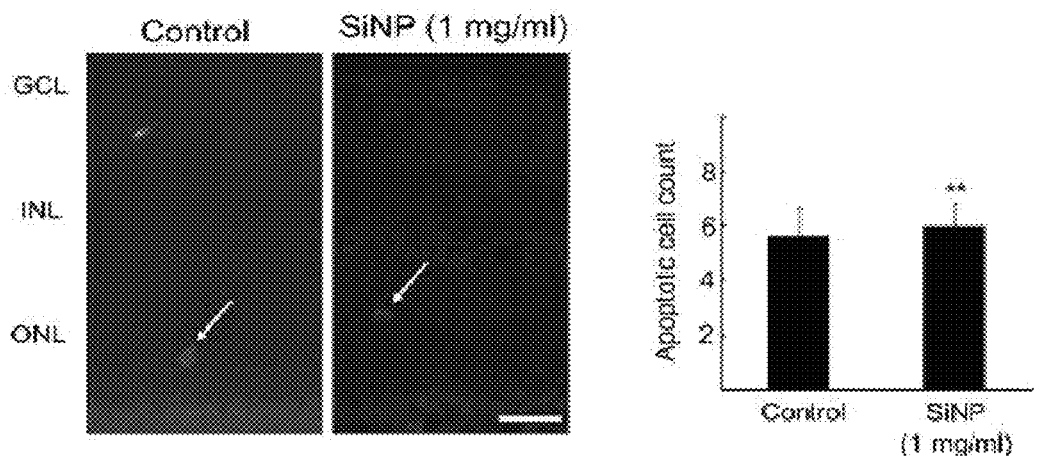

As a result, although it had been reported that the titanium oxide nanoparticles induce apoptosis depending on a treating amount thereof, it may be appreciated that the titanium oxide nanoparticles do not induce the apoptosis at a concentration of 1.30 μg/ml in the present invention. Further, the apoptosis was not generated at a concentration of 1 mg/ml of silica nanoparticles (See FIGS. 4A and 4B). That is, the level of apoptotic cell death in the retina did not change with the treatment of $TiO_2$ nanoparticles or silica nanoparticles of the present invention.

Furthermore, in order to analyze changes of retinal layer by the nanoparticles, a ratio between a thickness from an internal limiting membrane to an inner nuclear layer and a thickness from the internal limiting membrane to an outer nuclear layer was measured in all sections via a light microscope (Carl Zeiss, Inc., Chester, Va.). Through this measurement, changes in the retinal structure by the nanoparticles may be quantitatively measured.

Figure 5A:
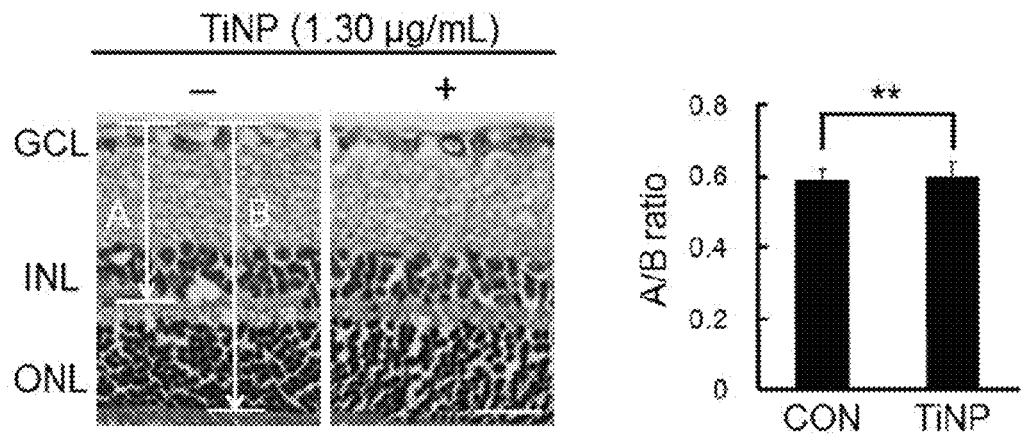
Figure 5B:
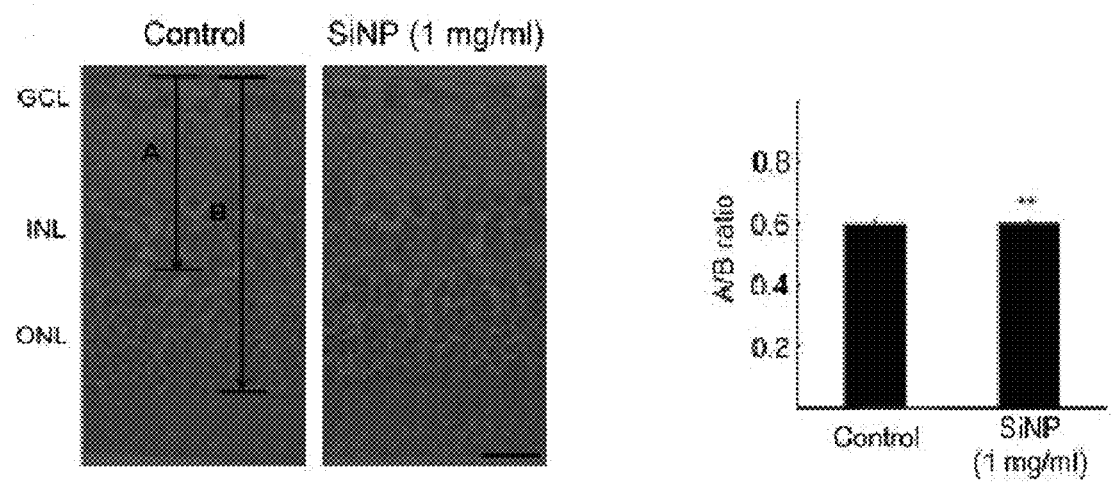
Figure 6A:
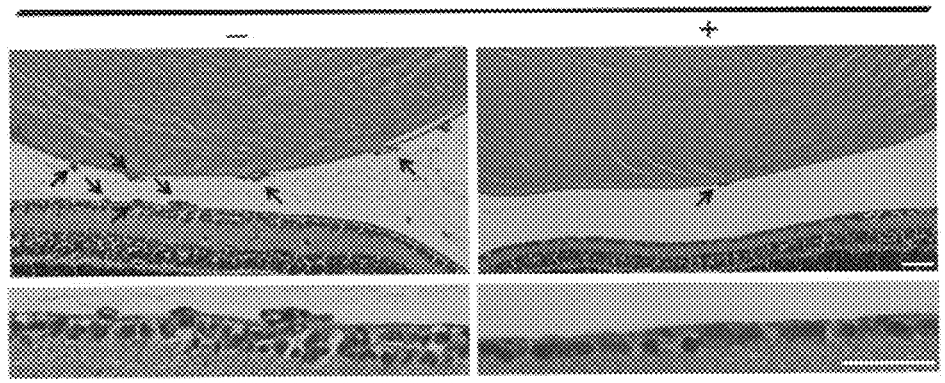
Figure 6B:
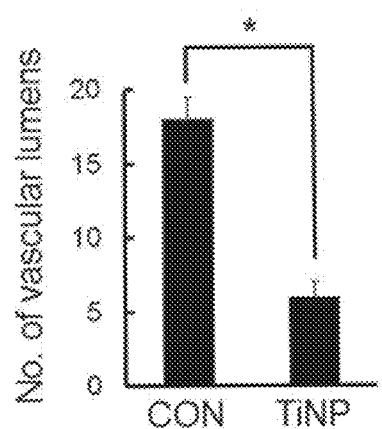
Figures 7A, 7B, 7C, 7D, 7E, 7F:
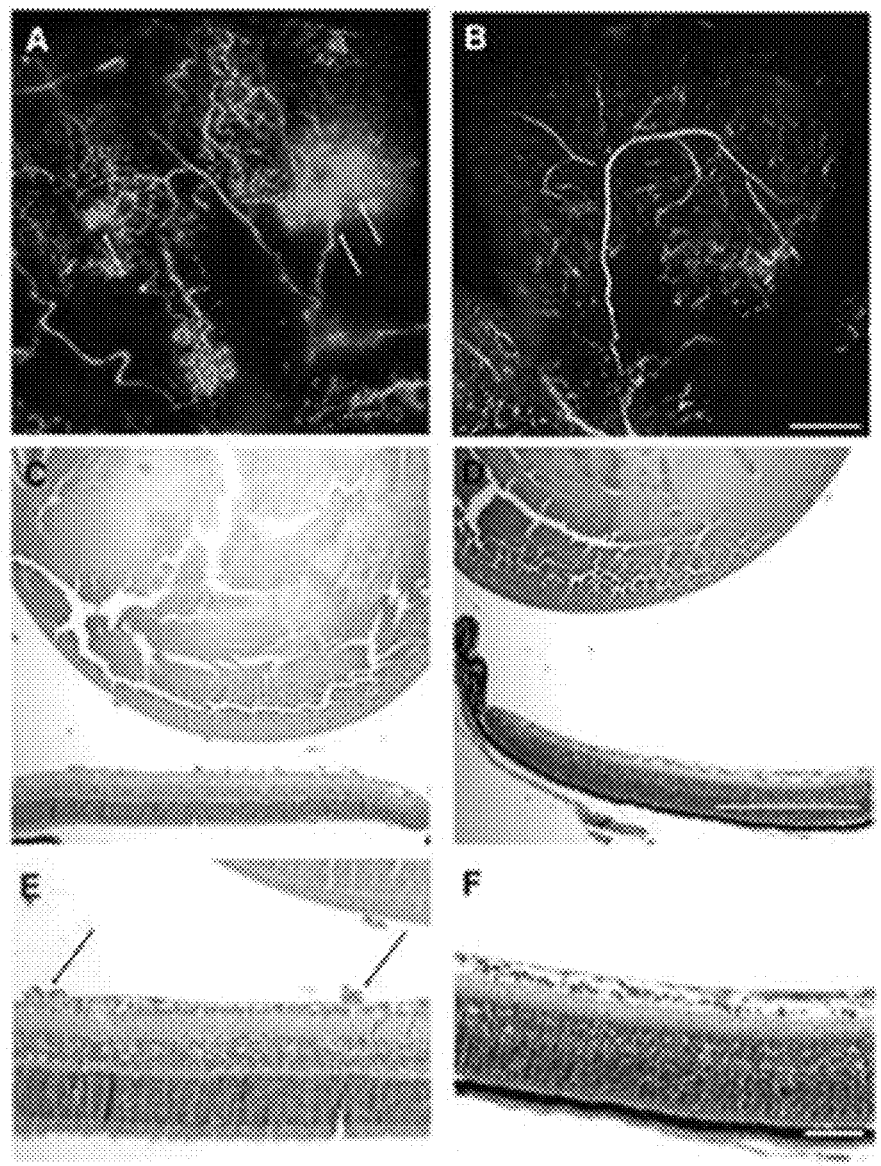
FIG. 7 is result confirming whether the silica nanoparticles have inhibitory effect on retinal angiogenesis in oxygen-induced retinopathy model. Here, A, C, and E are results for an OIR control mouse, and B, D, and F are results for a mouse injected with the silica nanoparticles.
Figure 7G:
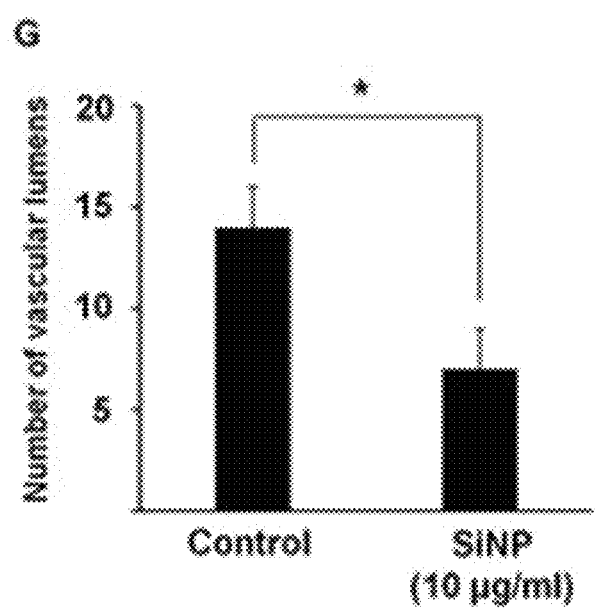
Figure 8A:
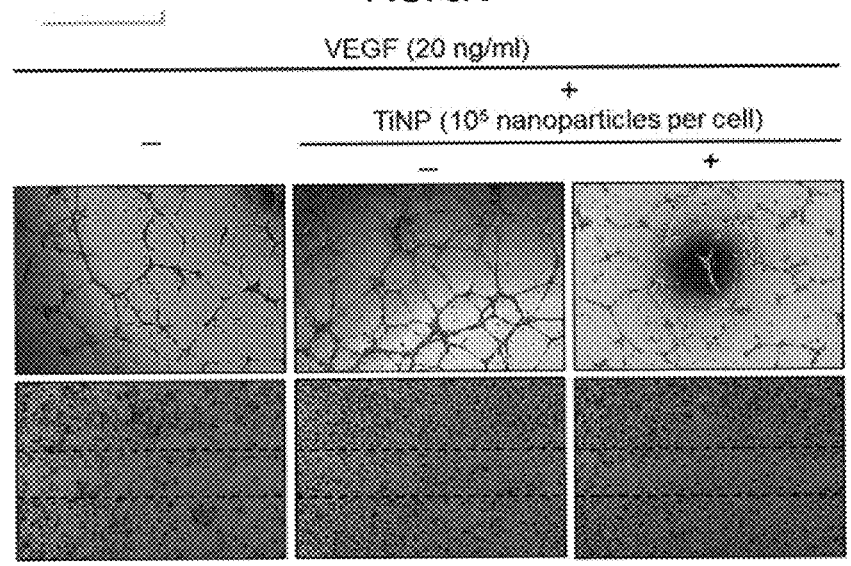
Figure 8B:
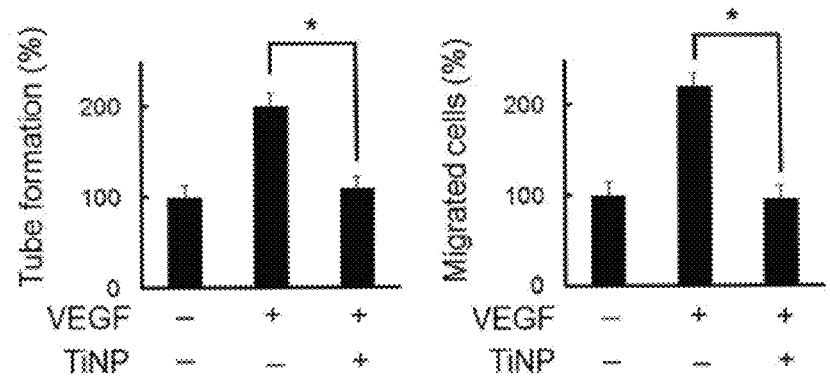
Figure 9:
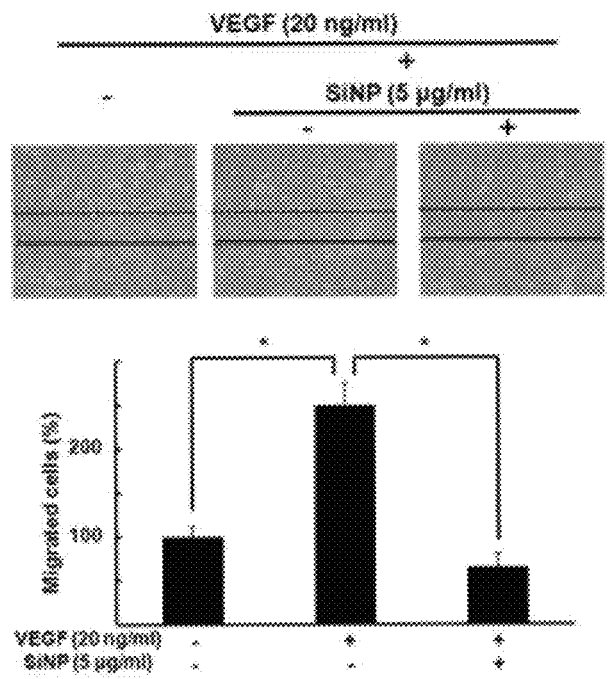
FIG. 9 shows wound migration assay of retinal endothelial cell of the silica nanoparticles.
Figure 10:
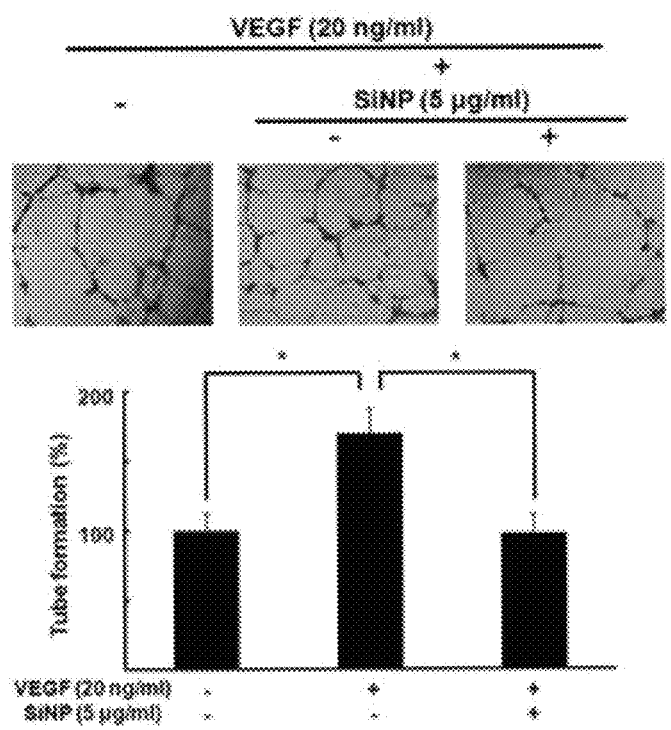
FIG. 10 shows tube formation assay of the silica nanoparticles.
Figure 11:
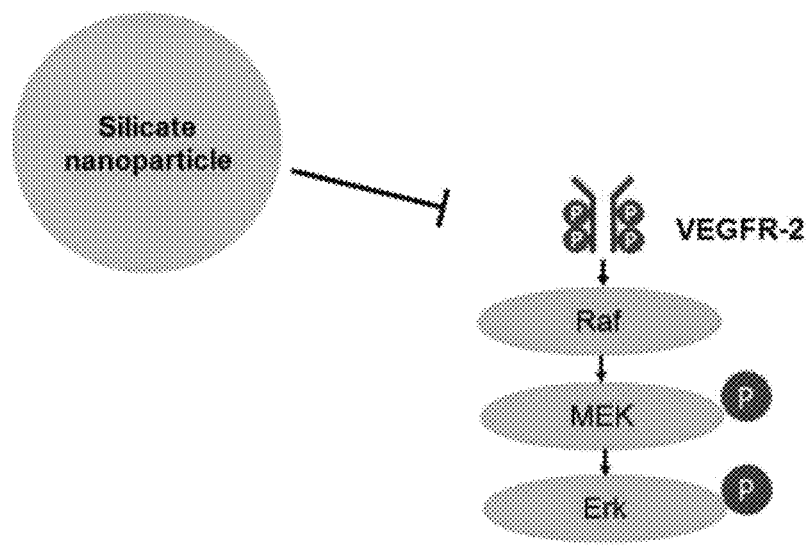
FIG. 11 is a view showing that the silica nanoparticles inhibit phosphorylation of VEGFR-2 and activation of ERK1/2, thereby inhibiting the retinal angiogenesis.
Figure 12:
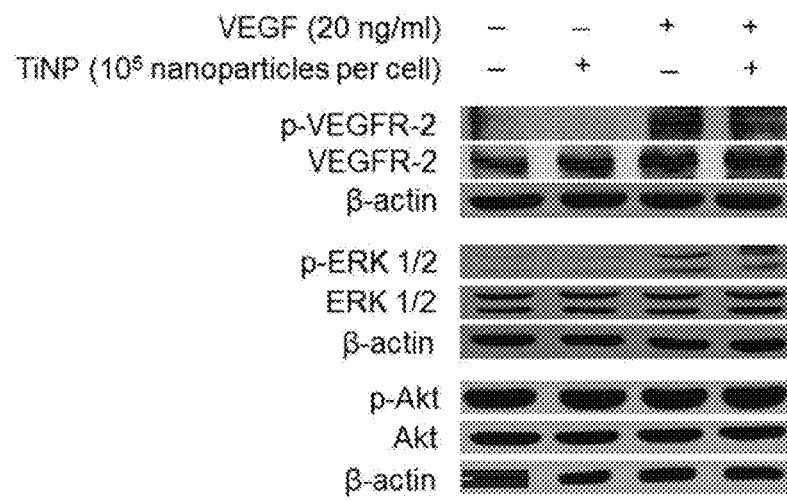
FIG. 12 shows western blotting results indicating that the titanium oxide nanoparticles inhibit the phosphorylation of the VEGFR-2.
Figure 13A:
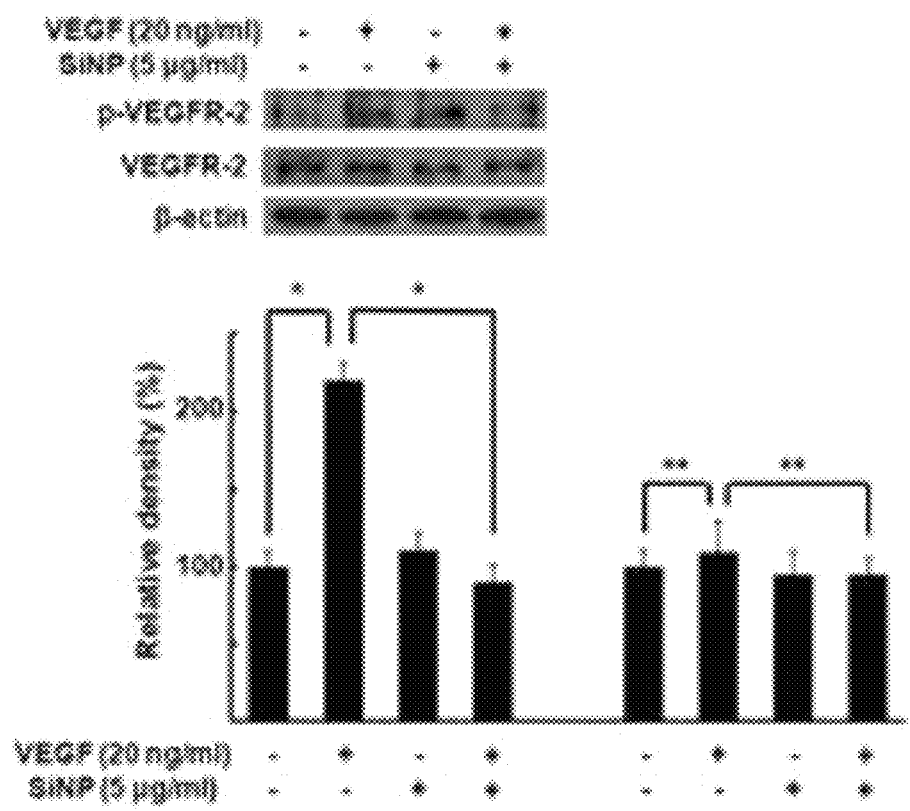
Figure 13B:
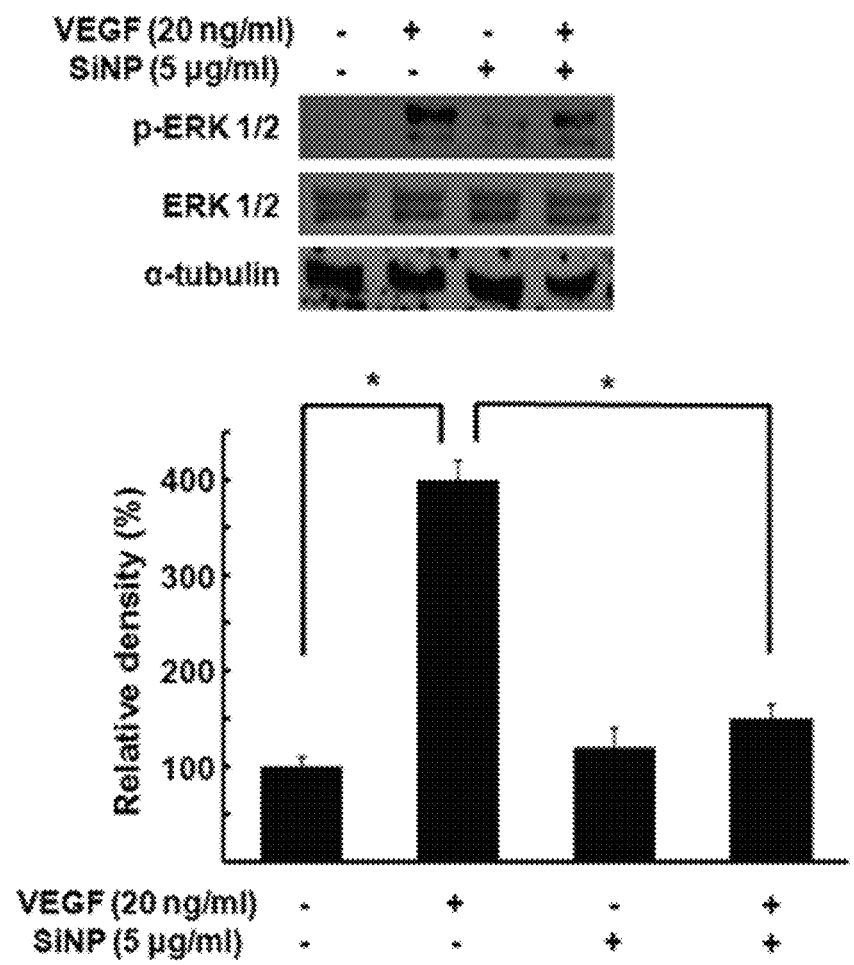
Figure 14:
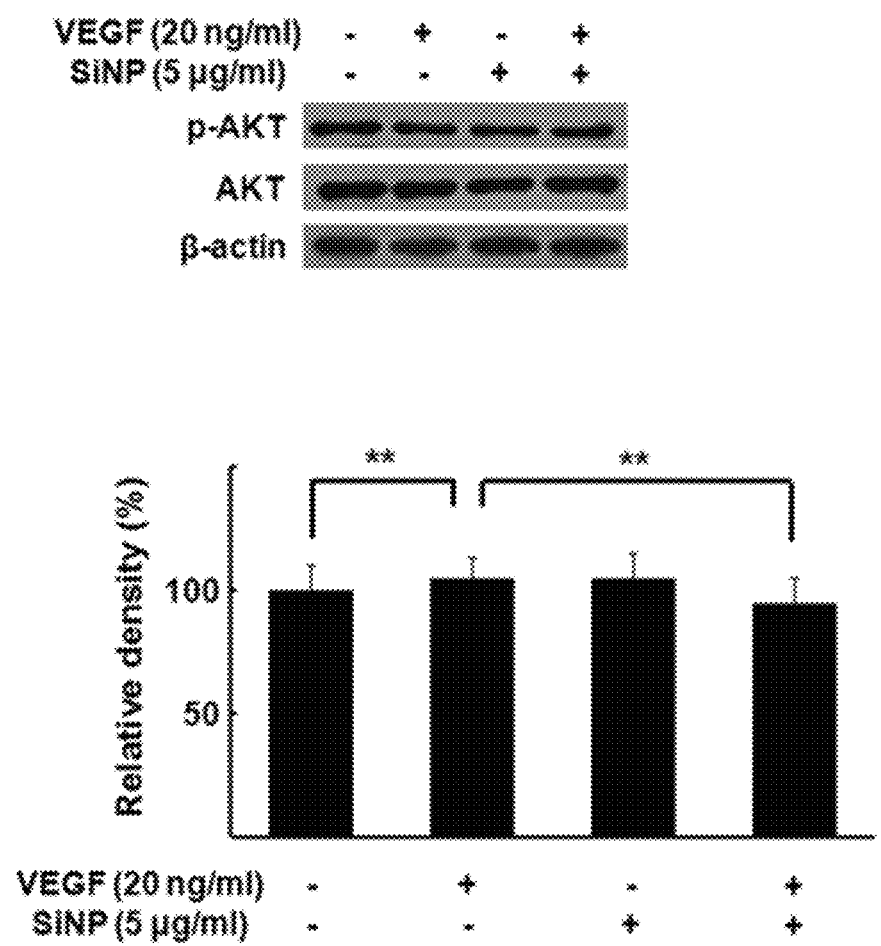
FIG. 14, which shows a western blotting result for Akt.

As a result, it may be appreciated that both of the $TiO_2$ nanoparticles and silica nanoparticles do not induce histopathological changes of the retinal tissue (See FIGS. 5A and 5B).

EXAMPLE 3

Confirmation of Anti-Angiogenesis Effect

1. Anti-Angiogenic Effect in an Oxygen-Induced Retinopathy Model

Oxygen-induced retinopathy (OIR) was induced by a method (Kim J H, et al. Deguelin inhibits retinal neovascularization by down-regulation of HIF-1alpha in oxygen-induced retinopathy. J Cell Mol Med. 2008; 12:2407-15) somewhat modified from the method described in Smith et al (Smith L E, et al. Oxygen-induced retinopathy in the mouse. Invest Ophthalmol V is Sci. 1994; 35:101-11). Newborn mice were randomly classified into a experimental group and a control group. 7 day old mice were exposed to hyperoxia for 5 days, and then returned to normoxia (room air) for another 5 days. The mice were treated with each of the titanium oxide nanoparticles and the silica nanoparticles at 14 days after birth, and eyes thereof were enucleated at 17 days after birth. As the inorganic nanoparticles, 10 μg/ml of SiNPs and 130.47 ng/ml of titanium oxide nanoparticles (1 μl PBS (phosphate buffered saline)) were intravitreally injected, respectively. The anti-angiogenesis effect was analyzed by a fluorescein angiography.

As a result, it may be appreciated that the titanium oxide nanoparticle effectively suppressed retinal neovascularization and formation of neovascular tufts is reduced by the silica nanoparticle treatment (See FIGS. 6A to 7G).

2. Influence on Angiogenesis In Vitro (Analysis Influence on Migration and Tube Formation of Endothelial Cell Migration of cells was analyzed by a wound migration assay on retinal microvascular endothelial cells. After HRMECs ($4\times10^5$ cells) were placed in the culture dish coated with gelatin at 90% confluence, and then were wound with a pipet tip. After wounding, the culture medium was replaced with a culture medium without a serum, and each cell was treated with $10^5$ titanium oxide and silica nanoparticles or 20 ng/ml of VEGF (Sigma-Aldrich Inc.) per a cell, followed by incubating for 12 hours. Then, the culture medium was removed, and the cells were fixed with absoulte methanol, then the cells were stained with Giemsa's solution (BDH laboratory Supplies, London, United Kingdom). The migration of cell was quantified by counting the number of cells migrated from the reference line using a light microscope (Carl Zeiss, Inc.) at a magnification of 200×.

In order to analyze the tube formation of the cells, the HRMECs ($4\times10^5$ cells) were positioned on a surface of Matrigel, and each cell was treated with $10^5$ titanium oxide and silica nanoparticles or 20 ng/ml of VEGF (Sigma-Aldrich Inc.) per cell, followed by culturing for 12 hours. The tube formation was quantified by counting the number of connected cells in the randomly selected field using an light microscope (Carl Zeiss, Inc.) at a magnification of 200×.

The angiogenesis means that proliferation and migration of the endothelial cells and formation of lumen are generated in the pre-existing blood vessels. It may be appreciated that the titanium oxide nanoparticle and silica nanoparticle inhibit migration that is increased two times or more by VEGF. In addition, it may be appreciated that the inorganic nanoparticle effectively inhibits the tube formation in the human retinal microvascular endothelial cells. It may be appreciated that the increase in the tube formation in the endothelial cells induced by VEGF is almost inhibited by the inorganic nanoparticle. As described above, the anti-angiogenesis effect of the titanium oxide nanoparticle and silica nanoparticle corresponds to previous anti-angiogenesis effects by gold, silica, silver nanoparticles (See FIGS. 8A to 10).

3. Analysis of Inhibitory Effect on Activation of VEGFR-2

In order to identify a molecular pathway of the anti-angiogenesis of the inorganic nanoparticle, western blotting was performed on protein playing an important role in a signaling pathway mediated by VEGF.

A concentration of the protein was measured by a BCA protein assay kit (Thermo Fisher Scientific Inc., Rockford, Ill.), and the protein was separated by a sodium dodecyl sulfate-polyacrylamide gel electrophoresis (SDS-PAGE, 6-7%), and the separated protein was transferred to a nitrocellulose membrane (Amersham Hybond™ ECL™, GE Healthcare, Cardiff, United Kingdom). The membrane incubated with primary antibodies, that is, anti-VEGFR-2 (Cell Signaling Technology, Beverly, Mass.), anti-phospho-VEGFR-2 (Cell Signaling Technology), anti-ERK 1/2 (Cell Signaling Technology), anti-phospho-ERK 1/2 (Cell Signaling Technology), anti-AKT (Cell Signaling Technology), anti-phospho-AKT (Cell Signaling Technology), anti-alpha-tubulin (Cell Signaling Technology), and anti-beta-actin (Cell Signaling Technology) for overnight at 4° C. Then, after the membrane was washed and treated with peroxidase-conjugated secondary antibodies (Cell Signaling Technology), the membrane was treated with Amersham ECL™ western blotting detection reagent (GE Healthcare), then was exposed to a film (Amersham Hyperfilm ECL, GE Healthcare). The results were scanned by a scanner, and intensity was analyzed by a TINA software program (Raytest, Straubenhardt, Germany).

It was known that the activation of VEGFR-2 by VEGF is required in a process of the angiogenesis. Therefore, whether inorganic nanoparticle treatment affects the phosphorylation of VEGFR-2 induced by VEGF was evaluated in the present invention. As a result, it was confirmed that the inorganic nanoparticle inhibits the phosphorylation of VEGFR-2 in HRMEC. In addition, it was confirmed that the phosphorylation of ERK1/2 induced by VEGF is effectively inhibited. However, the inorganic nanoparticle did not have any effect on phosphorylation of AKT.

The pharmaceutical composition containing inorganic nanoparticles selected from titanium oxide nanoparticles or silica nanoparticles as an active ingredient according to the present invention may be usefully used to prevent and treat the angiogenesis-related diseases by inhibiting cell migration and angiogenesis without toxicity in a specific concentration. Therefore, the metal and inorganic nanoparticles may be efficiently used as a therapeutic agent for various diseases based on angiogenesis such as age-related macular degeneration, tumors, and diabetes-related complications.

The exemplary embodiment of the present invention has been described above. Those skilled in the art will appreciate that the present invention may be implemented in a modified shape, without departing from the scope and spirit of the invention as disclosed in the accompanying claims. Therefore, the Examples described above should be considered in view of illustration rather than limitation. It should be interpreted that the scope of the present invention is defined by the following claims rather than the above-mentioned detailed description and all of differences within a scope equivalent thereto are included in the appended claims of the present invention.

What is claimed is:

1. A method for treating an angiogenesis-related disease, consisting of administering a composition consisting of nanoparticles as an active ingredient and at least one of a pharmaceutically acceptable excipient, a carrier, or a combination thereof into a body of a subject in need thereof, said nanoparticles consisting of titanium oxide and having a size of 28 to 60 nm,
    wherein the angiogenesis-related disease is selected from the group consisting of diabetic retinopathy and retinopathy of prematurity.

2. The method of claim 1, wherein the composition is administered in an amount of $10^5$ to $10^6$ nanoparticles per target cell in the subject.

3. The method of claim 1, wherein the composition is in a dosage form selected from the group consisting of liquid dispersions, gels, aerosols, ointments, creams, controlled release formulations, fast-dissolving dosage form, freeze-dried formulations, tablets, capsules, delayed release formulations, sustained release formulations, pulsatile release formulations, and a mixed immediate release and controlled release dosage form.

* * * * *